United States Patent [19]
Leader et al.

[11] Patent Number: 5,336,388
[45] Date of Patent: Aug. 9, 1994

[54] ANALYTE AND PH MEASURING SENSOR ASSEMBLY AND METHOD

[75] Inventors: Matthew J. Leader, Laguna Niguel, Calif.; Kee Van Sin, White Bear Lake, Minn.

[73] Assignee: PPG Industries, Inc., Pittsburgh, Pa.

[21] Appl. No.: 814,383

[22] Filed: Dec. 26, 1991

[51] Int. Cl.$^5$ ............................................. G01N 27/26
[52] U.S. Cl. ................................. 204/406; 204/403; 204/412; 204/415; 204/418; 204/419; 204/422; 204/433; 204/435
[58] Field of Search ............... 204/433, 416, 403, 435, 204/412, 406, 409, 415, 418, 419, 422; 128/635, 760, 766; 219/209, 121.6; 435/817

[56] References Cited

U.S. PATENT DOCUMENTS

| | | | |
|---|---|---|---|
| 3,000,805 | 9/1961 | Carritt et al. | 204/195 |
| 3,497,442 | 2/1970 | Vincent | 204/195 |
| 3,705,089 | 12/1972 | Grubb | 204/195 F |
| 4,706,678 | 11/1987 | Otten et al. | 128/635 |
| 4,818,361 | 4/1989 | Burgess et al. | 204/406 |
| 5,046,496 | 9/1991 | Betts et al. | 204/403 |

FOREIGN PATENT DOCUMENTS

| | | |
|---|---|---|
| 0306158 | 3/1989 | European Pat. Off. |
| 0351516 | 1/1990 | European Pat. Off. |

OTHER PUBLICATIONS

"Fluid Sample Analyte Collector and Calibration Assembly", U.S.S.N. 07/721,028, filed Jun. 26, 1991.
"Integrated Circuit Hydrated Sensor Apparatus", U.S.S.N. 07/721,025, filed Jun. 26, 1991.
"Electrochemical Sensor Storage Device", U.S.S.N. 07/721,027, filed Jun. 26, 1991.
"Electronic Wiring Substrate", U.S.S.N. 07/721,030, filed Jun. 26, 1991.
"Cathode in a Layered Circuit and Electrochemical Cell for Measurement of Oxygen in Fluids", U.S.S.N. 07/624,948, filed Dec. 10, 1990.

*Primary Examiner*—John Niebling
*Assistant Examiner*—Bruce F. Bell
*Attorney, Agent, or Firm*—Kenneth J. Stachel

[57] ABSTRACT

The sensor apparatus of the present invention includes on a nonconducting substrate electrically conductive pathways leading to at least two analyte electrodes and one reference electrode. The analyte electrodes each have sensitivities for both analytes but each has a membrane and/or electrolyte that favors the conversion of ionic potential to electronic potential for a different analyte. The apparatus has an fluid circuit means for liquid contact between the electrodes so that electric signals can be sent by electric circuitry to an analyzing means. The analyzing means determines the values of the analytes from the following simultaneous relationships:

$$\text{delta } mVA1 = -SE1A1 \times \text{delta pH} - SE1A2 \times \log A2f/A2i \quad \text{Equation 1}$$

$$\text{delta } mVA2 = -SE1A2 \times \text{delta pH} - SE2A2 \times \log A2f/A2i \quad \text{Equation 2}$$

$$A2f = A2i \times 10^n \quad \text{Equation 3}$$

where $$n = \frac{[SE2A1 \times \text{delta } mVA1 - SE1A1 \text{ delta } mVA2]}{[-SE2A1 \times SE1A2 + SE1A1 \times SE2A2]}$$

$$A1f = \text{delta } mVA1 + \frac{SE1A2 \times \log A2f/A2i}{-SE1A1} + A1i \quad \text{Equation 4}$$

where:
delta mV = change in millivolts
A1 = first analyte
A2 = second analyte
E1 = electrode constructed to favor the first analyte
E2 = electrode constructed to favor the second analyte
SE1A1 = sensitivity of the electrode favoring the first analyte for the first analyte
SE1A2 = sensitivity of the electrode favoring the first analyte for the second analyte
SE2A1 = sensitivity of the electrode favoring the second analyte for the first analyte
SE2A2 = sensitivity of the electrode favoring the second analyte for the second analyte
f = final measurement
i = initial measurement.

20 Claims, 3 Drawing Sheets

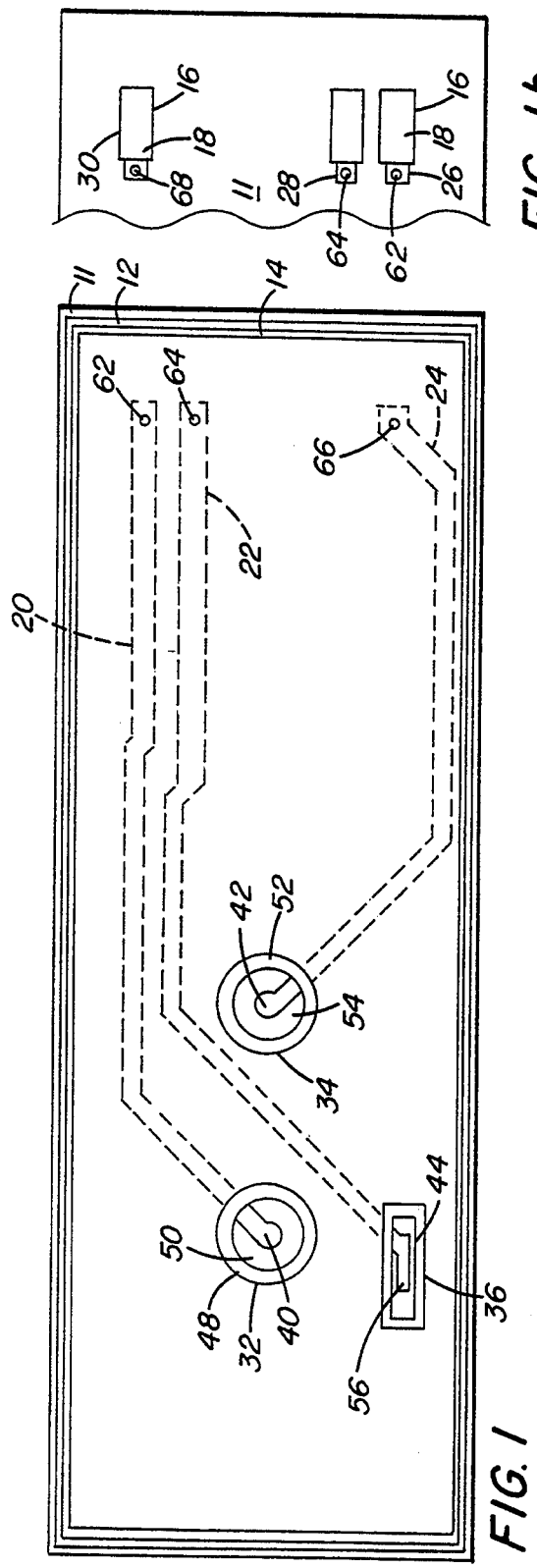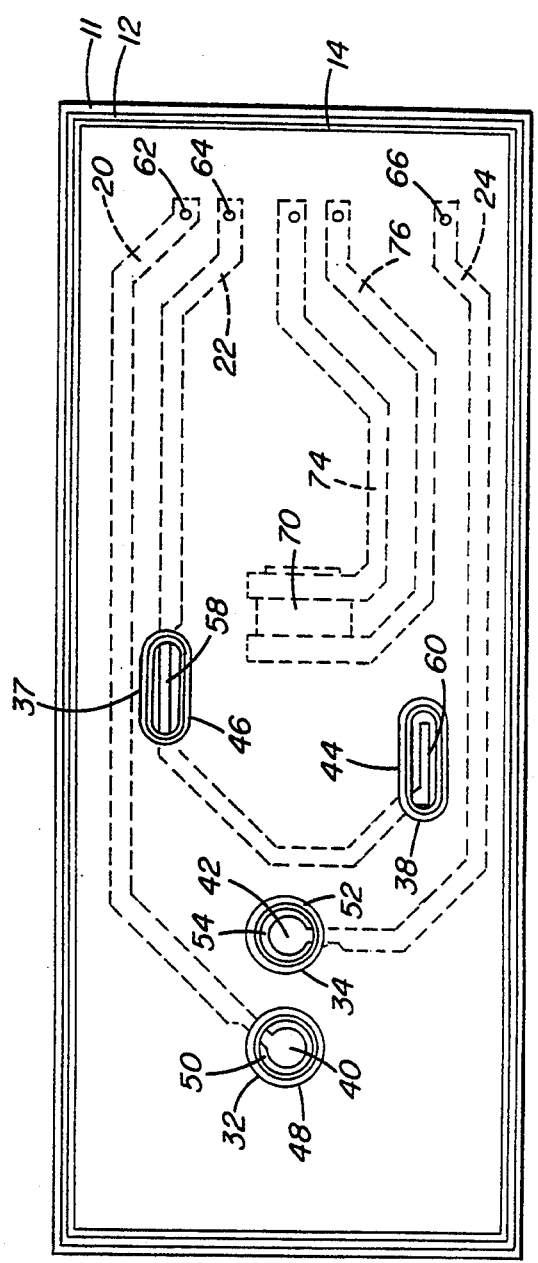

ANALYTE AND PH MEASURING SENSOR ASSEMBLY AND METHOD

The present invention is related to an analyte sensor assembly apparatus and method for measuring coupled analytes. More particularly, the present invention relates to an apparatus of a carbon dioxide and pH sensor assembly for measuring both in fluid samples.

BACKGROUND OF THE INVENTION

Numerous methods and apparatus exist in the art for measuring chemical components of fluids and current technology utilizes many types of sensors for detecting components and analytes in numerous types of fluids. For example, carbon dioxide and pH sensors are used for measuring these components in various fluids including gases and liquids. For instance, the measurement of blood gases, along with the pH from a sample of arterial blood, gives the state of the acid base balance or the effectiveness of both the respiratory and cardiovascular systems of the human or vertebrate body. Measuring the blood gases usually involves a measurement of the partial pressures of oxygen and carbon dioxide along with the measurement of the pH since carbon dioxide dissolved in the aqueous solution can affect the pH through the presence of carbonic acid. These are examples of coupled analytes.

It is conventional practice in many of the existing measurement methods, even where the fluid is a liquid or liquid with a dissolved gas with or without the presence of solids to transport a sample to a central location for testing. With centralized testing, the bulky, stationary, elaborate and sophisticated equipment performs the analysis on a practically endless number of samples. Originally, this equipment employed carbon dioxide sensor like the Severinghaus potentiometric sensor for a qualitative and/or quantitative measure of carbon dioxide. This sensor has a gaspermeable membrane between the sample solution for measurement and the measuring cell. The cell has a pH-sensing glass electrode, a reference electrode, and an intermediate electrolyte layer. Recently, more sophisticated carbon dioxide sensors have utilized polymeric membranes like those of the combined pH and carbon dioxide sensor of U.S. Pat. No. 4,818,361.

Also, recent attempts have been made to introduce more portable equipment into the marketplace of fluid analysis. An example of this is the qualitative and/or quantitative measurement of constituents or analytes of blood. The bulky stationary equipment is fairly expensive and the procedures for its use can be cumbersome depending on the type of fluid to be measured. For instance, measuring blood gases from the arterial blood sample involves: drawing the blood sample in a syringe, immersing it in ice and transporting it quickly to the lab where the equipment is usually located for a measurement of the gases. More portable devices would shorten or overcome transporting the sample to the measuring equipment at a fixed location. For example, portable sensing units which can be coupled to a digital readout device would be useful at the patient's bedside in a manner similar to a way that temperatures are measured at the patient bedside.

U.S. Pat. Nos. 3,000,805 and 3,497,442 show two such devices. The former has electrodes located on a syringe plunger and the latter has electrodes placed on the syringe well to conduct the measurements. The electrodes of these sensors may be particularly sensitive to small sample volumes since they consume oxygen in their operation. In U.S. Pat. No. 5,046,496, Applicants' assignee describes and claims a portable blood gas sensor which includes sensors fabricated using a conventional silk screening process where the electrodes are screened on to a ceramic substrate. Typically, these electrodes have the conductor along with an electrolyte and analyte permeable polymeric membrane that covers the sensor. Some of these membranes may be hydratable membranes by water vapor permeation and they can be stored in a dry state and hydrated just prior to use as in U.S. Pat. No. 4,818,361. The more portable the equipment the larger the demand for the miniaturization of the electrodes that still produce precise outputs for the analyte concentration or tension.

SUMMARY OF THE INVENTION

It is an object of the present invention to provide a sensor apparatus that utilizes analyte electrodes where each electrode has sensitivities for the analytes to be measured and where the analytes are water soluble analytes that upon solubization in water can influence the pH.

The sensor apparatus has in its broadest aspect a holding means for electrodes and for electronic conductive patterns at least two analyte electrodes, at least one reference electrode, a fluid circuit means in fluid contact with the electrodes, analyzing means, and the electrical circuitry means.

The at least three electrodes are held by the holding means in spaced apart relationship to each other and in electrical connection with electronic conductive patterns of the electric circuitry means which is also held by the holding means in insulated fashion for conveyance of electrical signals from the electrodes.

The analyte electrodes have ion selective membranes and/or a particular electrolyte composition that is selected to favor the conversion of the ionic potential to electronic potential of one analyte over the other. Each electrode has a sensitivity of the analytes to be measured but the sensitivities are different in each electrode. Both of the ion selective membranes have a first and second side and the membranes are positioned in the respective electrodes for one side to be in contact with the electrolyte of that electrode and for the other side to be available for exposure to the fluid circuit. The fluid circuit can have a storage fluid, hydrating fluid, analyte-containing fluid, or calibration fluids for analysis or a mixture of two of these. Additionally, the membrane of each electrode holds the respective electrolyte in contact with the conductor of that electrode.

The reference electrode can be an electrochemical half-cell or second order electrode that is provided in order to establish a substantially accurate and constant comparative potential. The reference electrode either with or without a membrane can have as an electrolyte the fluid that is in its vicinity in the fluid circuit means. Additionally, the electrolyte can include a metal cation of the electrode.

The electrodes are arranged further on the holding means to match the fluid circuit means so that the membranes of the analyte electrodes can contact the fluid in the fluid circuit. In this arrangement the analyte electrodes can contact the storage fluid, hydration fluid, calibration or standardized fluid, sample fluid, or all of these at different times when they are present in the fluid circuit means. The reference electrode can also contact one or more of these fluids either in axial or in nonaxial alignment with the analyte electrodes. The contact can be from channels or conduits having the fluid in a flow-through or nonflow-through fluid circuit means. The channel or channels can be in a cover encompassing the holding means for the electrodes or on a holder or card that slides into a recording instrument that has the electrodes held in a stationary position for the contact.

The electric circuitry means can be printed wire circuitry for the portion that is held by the electrode holding means. This electronic conductive pattern means portion of the circuitry allows for electrical connection of the electrodes to each other through one connection and for conveyance of the electronic potential to the analyzing means. Another portion of the electrical circuitry means can be a cable to convey electrical impulses from the holding means to the analyzing means.

The analyzing means receives digital or analog input and produces digital and/or analog output from the input via the simultaneous solution of the following equations:

$$\text{delta } mVA1 = -SE1A1 \times \text{delta pH} - SE1A2 \times \log A2f/A2i \quad \text{Equation 1}$$

$$\text{delta } mVA2 = -SE1A2 \times \text{delta pH} - SE2A2 \times \log A2f/A2i \quad \text{Equation 2}$$

$$A2f = A2i \times 10^n \quad \text{Equation 3}$$

$$\text{where } n = \frac{[SE2A1 \times \text{delta } mVA1 - SE1A1 \text{ delta } mVA2]}{[-SE2A1 \times SE1A2 + SE1A1 \times SE2A2]}$$

$$A1f = \frac{\text{delta } mVA1 + SE1A2 \times \log A2f/A2i}{-SE1A1} + A1i \quad \text{Equation 4}$$

where:
- delta mV = change in millivolts
- A1 = first analyte
- A2 = second analyte
- E1 = electrode constructed to favor the first analyte
- E2 = electrode constructed to favor the second analyte
- SE1A1 = sensitivity of the electrode favoring the first analyte for the first analyte
- SE1A2 = sensitivity of the electrode favoring the first analyte for the second analyte
- SE2A1 = sensitivity of the electrode favoring the second analyte for the first analyte
- SE2A2 = sensitivity of the electrode favoring the second analyte for the second analyte
- f = final measurement
- i = initial measurement.

In a narrower aspect of the present invention, the first analyte is the hydrogen ion concentration so that the first analyte electrode is a pH electrode. The second analyte is a carbon dioxide and the second analyte electrode is a carbon dioxide electrode. The electrode holding means is a nonconducting substrate suitable for attachment of the pH, carbon dioxide, and reference electrodes spaced apart from each other and connected to printing wiring circuits for conveyance of the electronic potential from the electrodes to the analyzing means.

BRIEF DESCRIPTION OF THE DRAWINGS

FIG. 1 is a top planar view of the one side of the substrate or wiring board of the present invention, having an arrangement of two analyte sensors with one reference electrode with accompanying electronic conductive patterns of the electric circuitry, and FIG. 1b shows a portion of the opposite side.

FIG. 2 is a planar view of the one side of the substrate or wiring board of the present invention having two analyte sensors (one analyte and pH) with two reference electrodes spaced apart from each other and from the axis of the analyte electrodes and accompanying electronic conductive patterns and also having a thermistor.

DETAILED DESCRIPTION OF THE INVENTION

Figure 2B:
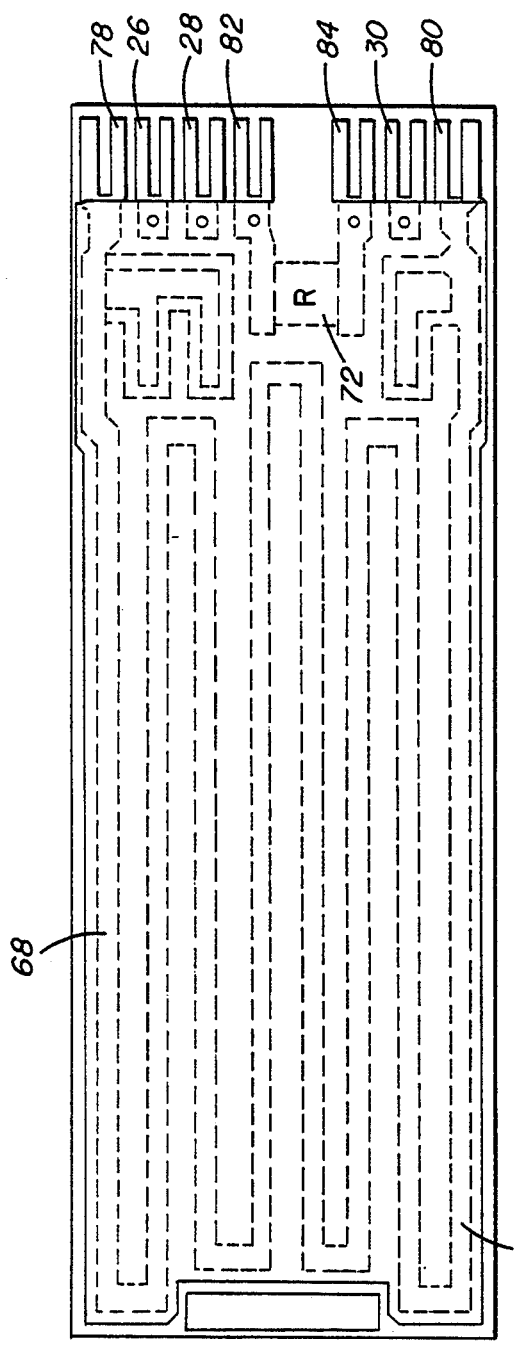
FIG. 2b is a planar view of the other side of the wiring board (substrate) of FIG. 2 having a resistor and a heater that traverses the board and a number of leads through the board from the side depicted in FIG. 2 to provide an external electrical connection from the board.

Similar numerals are used throughout the drawings to denote the same feature in each of the drawings.

The holding means 11 with electrodes and the associated portion of the electrical circuit means of the electrochemical sensor apparatus of the present invention as shown in FIG. 1 have particular shapes for the components. Other shapes than those shown in FIG. 1 that are known to those skilled in the art for the particular components can be used.

The electrode and circuit holding means 11 may be produced from any number of well known layered circuit technologies as, for example, thick film, thin film, plating, pressurized laminating and photolithographic etching or a combination of two or more of these; however, the thick film technique is preferred for all of the components. Of course it would be possible to produce the analyte electrodes by thick film process and the reference electrode by thin film process. The holding means 11 can be of any shape adequate to hold the electrodes and electric cicuit; one suitable example is a printed wire board substrate.

The holding means, hereinafter in the specification referred to as the substrate, 11 can be any glass or ceramic including sheet or chip or nonconducting substrate like wood or nonconducting polymers or commercially available frit that can be used as the substantially smooth flat surface of the substrate layer 11. Nonexclusive examples include borosilicate glass as is known to those skilled in the art for producing thick film or layered circuits. A nonexclusive and preferred example of which includes a ceramic base having around 96% Al2O3 such as that available commercially from Coors Ceramic Company, Grand Junction, Colo. The substrate layer 11 can be and preferably is essentially flat with two sides and any substrate known to those skilled in the art for forming printed wiring circuits can be used. It is preferred that the composition of the substrate can endure the presence of electrolytes that have acidic or basic pH and remain unaffected for a substantial period of time.

Substrate 11 can have several layers to form the electrodes and associated circuitry. One layer is a patterned metallic layer 12 with a number of extensions which act as the electric conductive pattern portion 18 of the electrical circuit means, collectively referred to as 22, between a voltage or current source (not shown) that is external to the substrate 11. Each extension can have a component (electrode conductors) at its end. The several extensions also have the ability to transmit voltage changes from the components of the substrate 11 to the analysis means (shown in FIG. 4).

The patterned metallic layer 12 is formed by printing pastes deposited onto a substrate in the desired pattern to act as ohmic conductors. Nonexclusive examples of suitable heat resisting metals include: noble metals such as platinum (Pt), ruthenium (Ru), palladium (Pd), rhodium (Rh), iridium (Ir), gold (Au) or silver (Ag) or other metals traditionally used in Severinghaus potentiometric sensors. A nonexclusive but preferred example of a suitable paste is a silver paste of the type produced and available from Electro-Science Laboratories, Inc. under the trade designation ESL 9912. The metallic layer 12 is dried to produce the above noted conductive pattern 18 which comprise the conductive pathways 20, 22, and 24 of FIGS. 1 and 2 and the external leads 26, 28, and 30 of FIG. 1b. Any method known to those skilled in the art for producing a sufficient thickness of metallic tracing can be used. Preferably, the silver pastes are oven dried and fired at a high temperature in a furnace. Firing can be accomplished at a temperature in the range of around 800° C. to around 950° C. for a period of around 1 to 20 minutes. With this procedure, the thickness of the layer of the metallic conducting tracing is usually in the range of around 0.0005 to 0.001 inches. Although the aforementioned are preferred conditions, general conditions for obtaining a proper thickness can be used where the thickness can be generally range from about 0.0004 to 0.0015 inch.

The aforementioned conductive patterns 18 are encapsulated with a glass ceramic mixture or a ceramic insulating material such as alumina or spinal. This encapsulation insulates the pathways and can range from a total encapsulation to encapsulation except at the end of the metallic pattern.

The encapsulation of the metallic patterns can range from encapsulating each from the other to a sufficient degree for electrical insulation of the conductive patterns and any conductive layers from each other. As shown in FIG. 1, the encapsulant can extend across the whole board from edge to edge as generally shown at numeral 14. Preferably, the thickness of the encapsulant layer is that which is adequate to seal the underlining metallic layer and to provide insulation for the metallic patterns. Preferably, the thickness of the layer is around 20 to around 30 microns. Preferably, the glass composition for the encapsulant as with the substrate 11 is selected to possess good chemical stability and/or moisture resistance. Also, the metallic and encapsulant materials are selected so that they can endure the presence of an electrolyte in a similar manner as the substrate composition. A most preferred glass ceramic mixture useful as the encapsulant is the type produced and available from Electro-Science Laboratories, Inc. under the trade designation ESL 4903.

As can best be seen in FIGS. 1 and 2, the substrate 11 is provided with a number of electrodes, 32, 34, 36, and 38, and more particularly, electrodes useful in the measurement of a fluid analyte that is soluble or dissociates in liquid, for instance water, to influence the pH of the liquid. A suitable example is carbon dioxide in a fluid like blood in the measurement of blood gases. Other analytes include those that are water soluble or dissociate in water and upon solubilization or dissociation influence the pH of water in a measurable manner. Nonexclusive examples of such analytes include: carbon dioxide, ammonia, sulfur dioxide, nitric oxide, and halides like chlorine, bromine, and iodine, and acids which do not dissolve in water to form a hydrogen ion but which have more than a certain degree of vapor pressure, like acetic acid, ammonia gas. This association of analytes with the pH is hereinafter referred to as coupled analytes.

The aforementioned electrodes 32, 34, 36, and 38 are preferably produced by one of the layered circuit techniques. This involves leaving the respective shaped ends uncovered while the rest of the metallic patterns are completely covered by the encapsulant. The conductors 40, 42, and 44 of FIG. 1 and in addition 46 of FIG. 2 may be masked during the encapsulation to keep them suitably uncovered by the encapsulant for the addition of active materials (e.g. electrolytes and polymeric membranes) to produce the electrodes on the surface of the substrate layer 11. This process involves masking the electrodes by the use of a polymer film coating on the screen used to screen print the encapsulant. This leaves the underlying silver exposed to form the conducting portion of the analyte and reference electrodes and the conducting pattern 18 on the substrate 11. It is also possible to use multiple layers of the metallic conductive layer and/or encapsulant, and the outer layer of the encapsulant may be solvent or thermoplastically bondable and may include polymers, as for example, acrylates or polyvinyl chloride as the major component in the encapsulant. The purpose of the outer coating or encapsulant is to enhance bonding of the active materials and, in particular, to provide a reliable surface for the attachment of the liquid or solid film type membrane materials. The geometry of the several electrodes could be made by a laser beam to carve or cut or trim the electrode; however, they are preferably prepared by the aforementioned layered circuit technique.

Each of the analyte electrodes are fabricated with electrolyte and membranes to perform their specific task and may be selected from many commercially available electrode components. The two analyte electrodes 32 and 34 on the substrate 11 in FIGS. 1 and 2 are prepared to maximize the electronic response from one of the analytes to be measured over the other. Either one or both of the membrane 48 and electrolyte 50 for electrode 32 are constructed to favor to some degree the conversion of the ionic potential of one analyte to an electronic response for the electrode. Membrane materials known to those skilled in the art are selected to enhance the permeability of the one analyte over the other and/or electrolyte materials known to those skilled in the art are selected in favor of the one analyte over the other. For the latter the electrolyte can be buffered to minimize the ionic potential of the other analyte while the desired analyte's ionic potential is favored. The membrane 52 and/or electrolyte 54 for electrode 34 can be selected in a similar manner to favor the conversion of the ionic potential to electronic potential for the analyte not favored by electrode 32.

In the preferred embodiment of the present invention in accordance with both FIGS. 1 and 2, one electrode, for instance, 32 is a pH electrode and the other electrode 34 is a $CO_2$ electrode. Each electrode is fabricated with a membrane which maintains their respective electrolytes in a fluid tight manner in the cavities or openings in which the electrodes are positioned. The pH electrode 32 and the $CO_2$ electrode 34 may be similar in regards to the circuit geometry and electrolyte and may be provided with membranes suitable for the particular characteristic being measured.

Electrode 32, preferably, a pH measuring electrode, has an electrolyte 50 in contact with the conductor 40. The electrolyte preferably has an acidic pH in the range of around 3 to around 4. A suitable acid electrolyte is an aqueous solution of potassium hydrophosphate ($KH_2PO_4$). A most suitable and preferred aqueous electrolyte is one from 13.6 grams of potassium hydrophosphate in one liter of deionized water. Preferably, the membrane for the pH electrode is a polyvinylchloride polymer, which is plasticized, and has the ionophore and the anion blocker. This membrane is prepared as the dried residue of a solution having the polyvinylchloride polymer which is a very high molecular weight polymer having a molecular weight in the range of around 10,000 to around 500,000 weight average molecular weight. Preferably, the plasticizers are o-nitrophenyl octyl ether (NPOE) and bis-(ethylhexyl)adipate or di-2-ethylhexyladipate (BEHA) and the ionophore tridodecylamine and the potassium tetrakis chlorophenylborate (KTClPB) anion blocker in the cyclohexanone solvent. The use of the very high molecular polyvinylchloride polymer reduces the permeability of the membrane to carbon dioxide. The acidic electrolyte suppresses the reaction of the carbon dioxide and water to minimize the extent to which the carbon dioxide changes the pH. This favors the electronic response for the pH measurement since the carbon dioxide produces little electronic response.

Electrode 34, which is preferably a carbon dioxide electrode, can have a membrane that is fabricated from a wide range of commercially available carbon dioxide permeable polymeric materials. As with the pH electrode, the electrolytes of the $CO_2$ electrode 34 is bound by its respective membrane. The electrolyte for the carbon dioxide sensor is initially at an alkaline pH in the range of greater than 7 to 14 and most preferably at a pH of around 8 with the presence of bicarbonate ions. A suitable formulation for the electrolyte is 0.02 moles of sodium bicarbonate in a liter of deionized water. The membrane for the carbon dioxide electrode holds the electrolyte in contact with the conductor; preferably, the membrane is water vapor porous and is made of a high molecular weight polyvinylchloride polymer that is plasticized and has the ionophore, tridodecylamine, in an organic solvent. A suitable membrane is produced from a polyvinylchloride powder which is a high molecular weight having a weight average molecular weight in the range of 10,000 to 500,000. Although this is the same range as for the pH electrode the molecular weight for the carbon dioxide electrode is lower than that for the pH electrode. The lower molecular weight polyvinylchloride membrane allows transport of the carbon dioxide through the membrane since it is more permeable to carbon dioxide. This PVC is plasticized with NPOE and BEHA in nitrobenzene with the presence of the ionophore. Preferably, KTCLPB is the anion blocker and cyclohexanone is solvent. The membrane most preferably is formed of the dried residue of the solution that has the following percentages by weight, high molecular weight, polyvinylchloride around 5, NPOE around 5, BEHA around 5, nitrobenzene around 5, tridodecylamine 1.78, potassium tetrakis (4-chlorophenyl) borate 0.9, and 76 cyclohexanone solvent. The carbon dioxide dissolves in the aqueous electrolyte and the pH changes so that the ionic potential of the electrolyte changes and this is converted at the conductor of the electrolyte to an electronic potential.

Although the aforedescribed pH and carbon dioxide electrodes were described as hydrated electrodes in that the electrolyte was an aqueous solution, the electrolyte can be a dried material or a gelled electrolyte. The dried electrolyte would require hydration prior to use through the membrane which is permeable to at least water vapor. In addition to the electrodes, other polymeric materials, plasticizers, ionophores, anion blockers and solvents can be used which are known to those skilled in the art. The materials should be used with electrolytes that favor maximizing the response of one analyte over the other for one electrode while maximizing the response for the other analyte in the other electrode. Nonexclusive examples of polymers for membranes that are permeable to carbon dioxide and other gases that are soluble in water and water vapor include cellulose acetate, polybisphenol-A carbonate (polysiloxane/poly(bisphenol-A carbonate) blocked copolymer; poly(methylmethacrylate), poly(vinylidene chloride), polystyrene, lower alkyl acrylate and methacrylate copolymers and polymers, polyurethane, and silicone rubber. Other suitable plasticizers are those like dioctyl adipate, tri(2-ethylhexyl) phosphate, dibutyl sebacate, diphenyl ether, dinonyl phthalate, dipenyl phthalate, di-2-nitrophenyl ether, glycerol triacetate, tributyl phosphate and dioctyl phenyl phosphate. An additional ionophore that can be used for hydrogen ion is trioctyl amine and for bicarbonate or total carbon dioxide quaternary ammonium ion exchanger p-octodecyloxy-m-chlorophenyl-hydrazone-mesaoxalonitrile (ocph). Where the analyte is ammonia, the ionophore can be nonacetine; where the analyte is nitrous oxide, the ionophore can be tridodecylhexadecylammonium nitrate plus normal octyl-o-nitrophenyl and other ionophores known for a specific analyte as known by those skilled in the art. Also, other polymers useful for forming membranes for hydrated electrodes are cation permeable and particularly hydrogen ion permeable membranes such as cationic exchange materials like copolymeric vinyl ethers as manufactured by E. I. duPont under registered trademark NAFION. Also other suitable hydrophillic polymers that can be used with solid electrolytes include: polyvinylalcohol, polyethylene oxides, polyethylene oxide ethers and various polysaccarides. Other examples of suitable solvents include: tetrahydrofuran (THF) and dimethylformamide (DMF).

The reference electrode 36 of FIG. 1 and 37 and 38 of FIG. 2 have conductor 56, 58, and 60, respectively. For this electrode, the electrolyte is present with or without a membrane and preferably without a membrane. The electrolyte can be is a storage, hydrating or calibrating solution which is a salt solution. The electrolyte for the reference electrode is basically a salt-bridge layer that acts as a source for a constant concentration of the measured ion species. This salt-bridge serves as an ion bridge between an analyte-containing solution and the reference electrode. It consists of small amounts of appropriate electrolytes dissolved in a water permeable hydrophillic polymer or water by itself. Additionally, other reference electrodes can be used which are in fluid contact with the analyte electrodes and suitable examples of such reference electrodes include that of U.S. Pat. Nos. 4,706,678 and 3,705,089, hereby incorporated by reference for their disclosure of reference electrodes.

As shown in FIG. 1b, which is a view of the opposite side from FIG. 1 where the substrate is flipped 180° about its longitudinal axis, the patterned metallic layer 12 has metallic external leads 26, 28, and 30 on the other side of the substrate 11. Preferably, there is one external lead for each conducting pathway 20, 22, 24. Although the external leads are shown on the opposite side of the substrate 11, they can also be on the same side or surface as their associated metallic lead patterns and components. External leads 26, 28, and 30 are conductively associated with the components on the FIG. 1a side of the substrate layer 11 through conductive holes 62, 64 and 66.

These holes may be drilled by a laser through the substrate 12 to conductively connect the conducting pathways 20, 22, and 24 traced on the FIG. 1 side of the substrate layer 11 with their respective metallic external leads 26, 28, 30 on the FIG. 1b side of the substrate layer 11. In general, these holes are produced by the focused laser beam drilling a hole by heating a small volume of material to a sufficiently high temperature for localized melting and/or vaporization. The holes can be drilled through the substrate layer 12 and when the metallic layers are screened such electrical connections are formed. Alternatively, the holes can be produced and preferably are produced by a very high powered carbon dioxide laser. This can be accomplished by the supplier of the nonconducting substrate and in this case the metallic layer is added to the substrate so each conducting pathway electrically connects with an external lead.

The external leads 26, 28, 30 may be produced on the other side of the substrate layer 11 with the same paste and firing as that done for aforementioned metallic patterns. The metallic external leads 26, 28, and 30 are in metallic electrical conducting contact with the various components on each side of the substrate 11. External lead 26 is in metallic electrical conducting contact with the pH sensing electrode 32; external lead 28 is in metallic electrical conducting contact with the $CO_2$ sensing electrode 34; external lead 30 is in metallic electrical conducting contact with one reference electrode 36 in FIG. 1 or two reference electrodes 37 and 38 in FIG. 2, which are located at the end of pathway 22.

The two analyte electrodes 32 and 34 and the one or more reference electrodes 36 and 37 and 38 are in spaced apart relation to each other and their conductors are insulated from each other but they are in a liquid junction electrical connection with each other. The membranes for at least the analyte electrodes and the electrolyte and any membrane that may be present in the reference electrode are in fluid contact with the fluid in the fluid circuit means 68 in FIG. 3. To assist in this liquid junction contact and electrical insulation of the electrical circuit pattern 18, the arrangement of the electrodes can exist in a variety of patterns on substrate 11. A preferred arrangement is that of FIGS. 1 and 2 where the pH electrode 32 is located at the end of extension 20; the other analyte sensing electrode 34 is located at the end of extension 22; and the one or more reference electrodes 36 in FIG. 1 and 37 and 38 in FIG. 2 are located at the end of extension 22. As noted in FIGS. 1 and 2, the two analyte sensors 32 and 34 are axially aligned along a longitudinal axis of the substrate 11. The one or more reference electrodes are located off of this axial alignment but can be located anywhere else on the substrate 11. This longitudinal axial alignment for the analyte electrodes 32 and 34 are for the preferred use of the sensor apparatus of the present invention. The preferred use is in a portable blood gas analyzer as further described in copending patent applications assigned to the same assignee as the present application, Ser. Nos. 07/721,028; 07/721,025; 07/721,030 and 07/721,027, all filed Jun. 26, 1991 and all of which are hereby incorporated by reference.

Alternatively, the sensor apparatus of the present invention if used in a different environment or device, the analyte electrodes 32 and 34 and reference electrodes 36 or 37 and 38 as in FIG. 2 could be positioned differently on the substrate 11. For instance, when the sensor apparatus of the present invention is utilized in a stationary device with samples inserted on a card or carrier to contact the electrodes the electrodes can be located anywhere on the substrate to match the location of the sample on the coupon or card. Their arrangement could even be in a straight line and the fluid circuit flow pattern might allow for a different fluid to be in contact with the one or more reference electrodes than with the two or more analyte electrodes.

Also shown in FIG. 2b, which is the reverse side of substrate 11, is heater 68 that is used in the preferred embodiment of the present invention to measure the concentration of the analyte at a temperature above room temperature. For example, when the fluid to be measured is blood or another bodily fluid, the elevated temperature is the normal body temperature of the vertebrate animal from which the blood was obtained. For control of heater 68, it is preferred to have present a thermistor 70 and resistor 72 arrangement as shown in FIGS. 2 and 2b. This arrangement makes it possible to indicate the temperature at any time on substrate 11 although it is also possible to have the heater, thermistor and resistor on the substrate of FIGS. 1 and 1b in a similar manner as in FIGS. 2 and 2b.

External leads 78 and 80 are in metallic electrical conducting contact with the heater 68 which is preferably a thick film heater provided on the FIG. 2b side of the substrate layer 11. The heater 68 can traverse the board in a serpentine fashion. External leads 82 and 84 are in metallic electrical conducting contact with a resistor 72 which is also provided on the FIG. 2b side of the substrate 11. The resistor 72 is in a half-bridge relationship with the thermistor 70 and, as such, it commonly shares external lead 82 with the thermistor 70, thermistor 70 also being in metallic electrical conducting contact with external lead 82. The function of the thermistor 70 and resistor 72 arrangement will be described below.

The serpentine formed heater 68 and the resistor 72 on the FIG. 2b side of the substrate 11 may be prepared by a number of commercially available techniques, however, they are preferably thick film devices prepared by the aforementioned layered circuit technique.

As before mentioned, external leads 78 and 80 are in metallic electrical conducting contact with the heater 72 and external leads 82 and 84 are in metallic electrical conducting contact with a resistor 72 which commonly shares external lead 82 with the thermistor 70; thermistor 70 also being in metallic electrical conducting contact with external lead 64.

Thermistor 70 is located at the end of conducting pathways 74 and 76, and is preferably a thick film thermally sensitive resistor whose conductivity varies with the changes in temperature. The thermistor 70 may be fabricated from a number of semi-conductive materials as, for example, oxides of metals. The thermistor may be formed and applied to the substrate 11 by the use of the aforementioned layered technique. The temperature coefficient of the thermistor 70 preferably is large and negative and is used to sense the temperature of the substrate 11 at all times when the substrate 11 is electrically connected via electric circuitry 16 to a power source and the analyzing means of FIG. 4. Thermistor 70 is operated at relatively low current levels so the resistance is affected only by the ambient temperature and not by the applied current.

Figure 4:
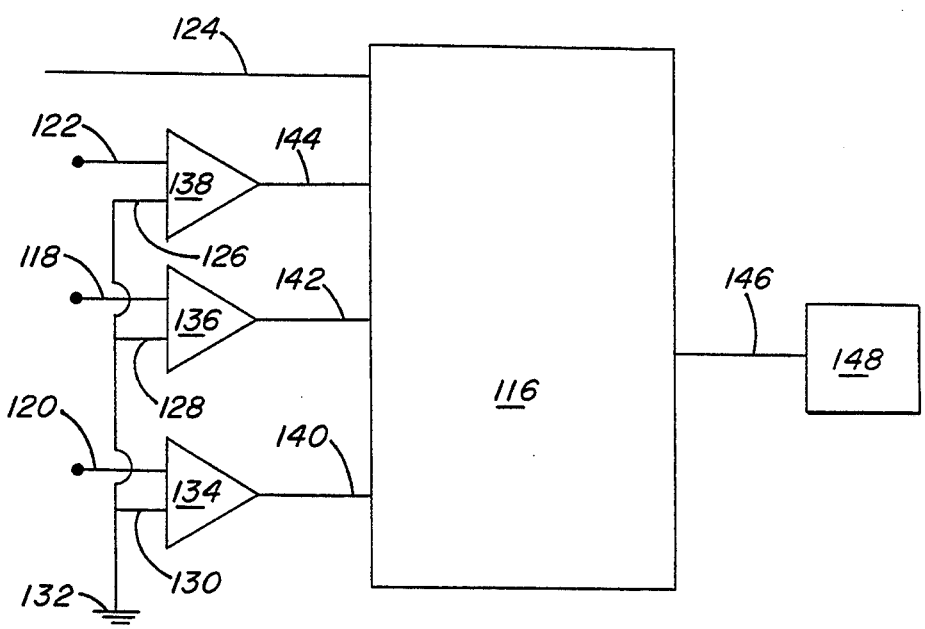
FIG. 4 is a schematic of the circuitry including the analyzing means.

The half-bridge circuit configuration involving resistor 72 preferably is a voltage divider and generates a ratiometric output to the analyzing means of FIG. 4. This is important for it allows the actual resistance values to float and results in highly consistent and accurate temperature sensing and control of the substrate 11 on a substrate-to-substrate basis. Accuracy and consistency of the resistor 72 and thermistor 70 arrangement is preferably achieved by calibrating the substrate 11 with conductive patterns by laser trimming of the resistor 72 to produce zero volts at 37° C. The laser beam is precisely deflected across the thick film resistor 72 to produce the desired temperature voltage relationship. A current is applied at external leads 82 and 86 by the analysis means of FIG. 4 with a power source until zero volts is achieved. This gives a linear output so that the temperatures can be measured other than 37° C. from the slope of the line from the calibration at room temperature and 37° C. The resistor 72 has essentially zero temperature coefficient and, accordingly, may be placed without any adverse effect on the sensing capability of the associated thermistor 70 on the FIG. 2b side of the substrate 11 with the heater 68.

Accurate sensing of the ambient temperature of the substrate 11 is required to precisely control the heater 74 to ultimately maintain, within a narrow distribution of temperatures, the desired operating surface temperature on the FIG. 1 or FIG. 2 sensor side of the substrate 11.

Placement of the thermistor 70 is another important aspect of the present invention. As can be seen in FIG. 2, the thermistor 70 is placed in the same plane and in close relation to the electrodes 32, 34, 37 and 38 to thereby accurately sense the ambient temperature at or near such sensors. This physical placement of the thermistor 70 allows for the rapid adjustment of the heater 68 by the analysis means of FIG. 4 with a power supply to maintain the desired operating temperature. The thermistor 70 and resistor 72 arrangement can provide temperature measurement accuracy of within 25° C. This physical placement of the thermistor 70, so close to the electrodes, requires that it be correctly fabricated to ensure that it is electrically isolated from the electrolytes of the several electrodes. The encapsulant for the thermistor 70 should be thick enough to accomplish the electrical isolation, yet thin enough so as not to lose any response time.

The heater 68, provided on the FIG. 2b side of the substrate 11, rapidly and accurately produces the necessary heat in response to any temperature change sensed by the thermistor 70; the thermistor 70 and the several electrodes preferably all being in the heated region produced by the heater 68. Thick film heaters are not generally considered to be rapid response devices and their heat output tends to take a relatively long time, in terms of electronic devices, to change. To improve the responsiveness of the heater 68, it can be powered by pulsed DC so that the heater is continually turned on and off by the analyzing means with power supply of FIG. 4. This not only increases the responsiveness of the heater 68 but also allows for better overall thermal control including avoiding the heater 68 from overshooting or undershooting the desired temperature.

Figure 3:
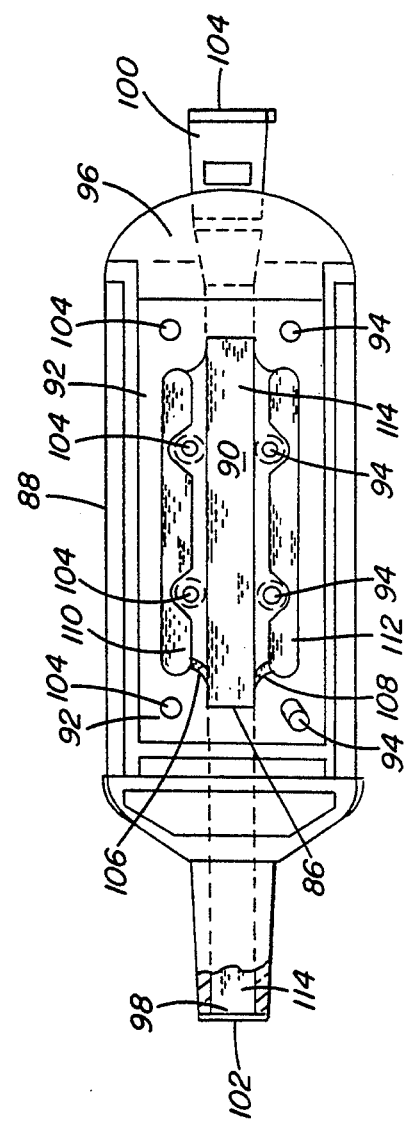
FIG. 3 shows a matching fluid circuit means for the substrate in FIGS. 1, 1b, 2 and 2b.

Whatever the arrangement of the electrodes on substrate 11, their arrangement is matched by a fluid pattern 86 which may be flow through or non-flow-through design. A suitable flow-through design, which is preferred, is shown in FIG. 3. The one or more fluids are continuous in the pattern to provide the liquid junction between the electrodes for electrical conductivity. Preferably, the fluid pattern 86 is occupied by at least two different fluids. Preferably, a storage fluid is in contact with the reference electrodes 36 in FIG. 1 or 37 and 38 in FIG. 2 while the fluid pattern 86 allows for contact of a storage fluid, hydrating fluid, if needed, calibrating fluid, and sample fluid for the analyte electrodes 32 and 34.

FIG. 3 shows a suitable cover 88 having one section to enclose or surround the substrate 11 with electrodes 32, 34, 36 and, in FIG. 2, 37 and 38 and conductive pattern 18. The cover 88 can be made of any fairly rigid moldable material such as rigid thermoplastic polymers although thermosetting polymers can also be used. A suitable example is a methyl methacrylate styrene butadiene terpolymer and rigid plastics such as polyesters like polyethyleneterephthlate or polycarbonate or blends or alloys thereof and other similar materials known to those skilled in the art. The cover 88 can be any basic geometric shape suitable for containing a channel 90 and substrate 11. The number of parts or sections comprising the cover can range from 1 to a plurality but two parts are preferred. A single part cover as shown in FIG. 3 has the substrate 11 forming one side like a backing to the cover 88 when the substrate 11 is positioned in the cover 88. Another possibility is for the cover 88 to have a first and second opposing sections where one section is the cover section and the second section is a back section. Each section has an exterior and interior surface and when both section are matched together, they completely encase the substrate 11.

The cover 88 by itself when the substrate 11 is the backing or the two sections of the cover when matched together form an interior space 92. Space 92 need not be of any particular geometric configuration just so long as substrate 11 fits into the space. The internal space 92 and substrate 11 are preferably of matched configuration and are preferably generally rectangular. Preferably, when the cover 88 has two sections, the top section with the fluid circuit pattern 86 comprises a substantial portion of the cover 88 as shown in FIG. 3 and the other is a backing for substrate 11. With this arrangement and with the internal space 92 having dimensions that closely match those of the substrate 11 for a snug fit of the latter into the former, and both sections can assist in providing electrical isolation between any fluid in the channel 90 and the electric circuit means 16. The former is at least in fluid pattern 86 and the latter is on substrate 11. This reduces the risk of leakage current or short circuiting of the conductive patterns 18 of the electrical circuitry means 16.

The cover 88 can be adhesively connected to a back, i.e. the substrate 11 or a backing for the substrate (not shown) to improve their attachment to each other through connection means 94. The cover 88 also can allow for communication from the conductive patterns 18 to an electrical connection means 96 which electrically connects the conductive patterns 18 to the analysis means shown in FIG. 4. The electrical connection means 96 in conjunction with the conductive patterns 18 comprise the electrical circuitry means 16.

Cover 88 in conjunction with the substrate 11 provides for at least one channel 90 to pass over at least one analyte electrode on substrate 11 and for any other channels to interconnect. Channel 90 is constructed to have any shape that allows for fluid flow to, over, and from the one or more electrodes and to allow for ingress and egress of fluid from the channel. The channel 90 can have two opposing openings to allow fluid flow through the channel from a receiving opening 98 to an exit opening 100, where the former is before and the latter after the electrodes. The receiving opening 98 can be suitable for attachment to a sample receiving means (not shown) and the exit opening 100 can be suitable for attachment to a collection means (not shown) such as a syringe or reservoir in general. Also, when the channel 90 is flow through and contains a fluid for storage or preconditioning, the openings 98 and 100 can be sealed by a substantially moisture impervious seal 102 and 104, respectively. The openings 98 and 100 can serve as an inlet to or outlet from cover 88 that is preferably formed by conical tips preferably aligned in the same plane and along the same axis at opposite ends of the channel 90. In this arrangement channel 90 passes longitudinally over the substrate 11. The interior space 92 of the covering communicates with the one or more channels to contain the substrate 11 so that the electrodes that are on the substrate are so disposed to lie in the path of the channel for fluid contact. The remaining portions of the channel 90 and any other channels are formed by substrate 11 occupying the internal space 92 so that the surface of substrate 11 with one or more electrodes actually forms a wall of the channel 90.

Seals 102 and 104 can have one or more surfaces where at least one surface is substantially a non-oxidizing metal such as aluminum that is useful with an adhesive-type polymer. The adhesive-type polymer can be used either as an application to the surface to be sealed or as another surface of the seal. The seal is fixedly attached to the housing by a chemical means and/or by a mechanical means.

Preferably, the cover 88 in conjunction with the substrate 11 provides for a plurality of channels. The number of channels for the fluid pattern 86 is sufficient that the analyte electrodes 32 and 34 are on one or more channels that are separate from the one or more channels for the one or more reference electrodes. This arrangement allows the reference electrodes as 36 and, for FIG. 2, 37 and 38 to have a different fluid in contact with them than the fluid in contact with the analyte electrodes 32 and 34. The fluid in contact with the reference electrodes can be a calibrating or hydrating fluid while a sample fluid is in contact with the analyte electrodes 32 and 34. With connecting channel sections 106 and 108 connecting side channels 110 and 112, respectively, with channel 90, the one or more reference electrodes of FIGS. 1 and 2, respectively, can be off the axial alignment with the analyte electrodes 32 and 34 and still be in liquid junction contact with them through the fluid circuit 86. The substrate 11 of FIGS. 1 and 2 can be positioned in the cover 88 so that the a reference electrode is in fluid contact with the fluid in one or both of the side channel 110 and 112. Concomitantly, the analyte electrodes 32 and 34 are in fluid contact with the fluid in channel 90. In an alternative embodiment, only channel 90 is present and all of the electrodes both analyte and reference contact the fluid in the channel 90.

The fluid occupying the portion or portions of the channel 90 or channels 90, 110 and 112 over the one or more electrodes can be a storage, hydrating or calibrant fluid. A storage fluid can range from air for electrodes with dried electrolyte to a liquid that has some amount of water although a minor quantity of organic liquids may also be present. Preferably, the fluid is a stable liquid for storage ranging from a short time (days or weeks) to prolonged periods of time of several months. Preferably, the fluid that occupies the fluid circuit 86 is an aqueous solution that is isotonic with any electrolyte in the one or more electrodes. More preferably, the fluid of the fluid circuit 86 in FIG. 3 can be a hydrating fluid that is also isotonic. Then the fluid can act as the electrolyte for any reference electrodes on the substrate 11 that do not have a membrane. The hydration fluid can be one that is added to hydrate solid or dried electrolyte in the electrodes or, preferably, to maintain the hydrated electrolyte in the electrodes. The hydrating fluid is chiefly an aqueous fluid with an effective composition to hydrate at least to a partial degree but better to a substantial degree the hydrophilic polymeric membranes. A suitable example of a hydrating fluid is an aqueous solution comprising: disodium hydrogen phosphate, potassium dihydrogen phosphate, sodium bicarbonate, and sodium chloride. Such a solution can have a varying range of amounts for the individual constituents but most preferably for the aforelisted salts the amounts are in millimoles per kilogram of water in the order listed as follows: 4.8, 13, 22, and 12.5. The quantity of hydrating fluid in channel 90 or the plurality of channels is at least that which is sufficient to cover or remain in contact with the one or more electrodes. This arrangement is more fully shown in a copending patent application Ser. No. 07/721,025, filed Jun. 26, 1991, assigned to the same assignee as this application and which is hereby incorporated by reference.

Any arrangement or configuration other than that shown in FIG. 3 can be used that allow the two sections to engage and form cover 88 with one or more internal spaces for placement of substrate 11 so that the electrodes are in fluid contact with any fluid 114 that is in the one or more channels. Other suitable arrangements include those described in European patent applications 0306158 and 0351516 and U.S. Pat. No. 4,818,361, all hereby incorporated by reference.

FIG. 4 shows the preferred electrical connection of the analyzing means 116 through the electric circuit means 16 to substrate 11. Electrical connections 118, 120, 122 and 124 are apart of the electric circuit means 16 and electrically connect with the appropriate external leads of the substrate 11. Preferably, connections 118, 120, 122 and 124 are part of one ribbon-type cable connecting the analyzing means 116 as a module to the external leads of the substrate through any electrical attachment means known to those skilled in the art. In such a ribbon cable, connections 118, 120 and 122 would be individual wires in the cable and connection 124 would be comprised of several individual wires in the cable. Connection 124 would include wiring for any power supplied to the substrate 11 or, heater 68, or thermistor 70 or resistor 72 or any other electrical components on the substrate 11. Also connection 124 could include wiring for conveying any additional electronic potentials from additional electrodes on the substrate 11 like an oxygen sensor which is preferably present and can generally be any oxygen microsensor known to those skilled in the art.

It is also preferred that the pH and $CO_2$ electrodes and the sensor apparatus of the present invention is used in conjunction with an oxygen electrode and sensor and the means 116 is capable of receiving input from these electrodes and reference electrodes for them and outputting data for pH, $CO_2$ and oxygen. The combination of the pH and $CO_2$ along with the oxygen sensing is as described further in pending the U.S. patent applications which are commonly assigned to the same assignee as the subject patent application having U.S. Ser. No. 07/721,030, filed Jun. 26, 1991, and 07/624,948, filed Dec. 10, 1990.

In FIG. 4 the electronic signal from one of the analyte electrodes, for example electrode 32, is conveyed by the electronic pathway 20 of FIG. 1 to the lead 26 of FIG. 1b to electrical connection 120 and to amplifier 134. Likewise, the signal for the other analyte electrode 34 is conveyed by pathway 24 to lead 30 to connection 118 and to amplifier 136. Also, the electrical signal from the one or more reference electrodes of the substrate 11 of FIGS. 1 or 2 is conveyed by pathway 22 to lead 28 to connection 122 to amplifier 138. The other connection for the amplifiers can go to ground 132 through connections 126, 128, and 130. The amplifiers can be any amplifying electronic component known to those skilled in the art and can actually be and preferably is apart of the analog input processing function of the analyzing means 116 rather than discrete components. The amplifiers are shown in FIG. 4 as discrete components mostly for illustrative purposes.

The analyzing means 116 receives separate electrical signals from the two analyte electrodes and the one or more reference electrodes, for example as depicted in FIG. 4 as signals 140, 142 and 144. The analyzing means 116 can be as simple as a voltmeter and calculating device or an electronic circuit board with suitable electronic components to perform the functions of analog input processing, analog to digital conversion, programmed microprocessing, and a date/time circuit and battery backup random access memory, and a power supply. In the preferred embodiment, analyzing means 116 also has the capability of battery power supply in addition to standard wall socket power supply. Preferably, the analyzing means is a self-contained, hand-held, preferably battery powered monitoring instrument or analyzer to process the signals and displays the information in a digital or paper mode to the operator. Also preferably in means 116, the analog input processing unit interfaces with a 12 bit analog to a digital converter which itself interfaces with an 8 bit programmed microprocessor. The processor accesses the date/time circuit and battery backup random access memory. Means 116 is electrically connected by connection 146 to a display device 148 that can be a digital or analog display with or without but preferably with a printer. Also means 116 preferably has a battery and charger assembly that provides battery power. Although a particular arrangement for the functional units of the means 116 has been specifically set forth, variations are possible that may delete one or more of the functional units. As long as the processing, memory, and converter are present when analog signals are used, and the processor is functionally tied into these units and power is supplied, a read out can be obtained.

Means 116 can be programmed in any language known to those skilled in the art like "C" where the program can reside on a floppy disk when means 116 has a floppy drive or and preferably can reside in firmware like a PROM or EPROM. The program allows means 116 to give two analyte concentration values from the electronic signals. The program takes the electronic response of the analyte electrodes compared to the reference electrodes along with sensitivities of the analyte electrodes and initial readings on fluids with known values of analytes to determine the unknown analyte values. The determination is according to relationships derived from the Nernst and Henderson-Hasselbalch equations. With the known analyte value, like that for carbon dioxide in a calibrating fluid, the analyte electrodes, like carbon dioxide and pH electrodes, can be calibrated. Both of these electrodes have a certain sensitivity in millivolts per millimeters of mercury for carbon dioxide tension. This is determined via a statistical process by measuring many samples which are compared against the sensor being checked. Means 116 checks or predicts the millivolt change from the millivolts measured for the one or more calibrant fluids and this change should be within the statistical range of acceptable values or the sensitivity of the sensor is not within specifications. This tests the sensitivity of the electrodes to determine if they are accurate.

Figure 5:
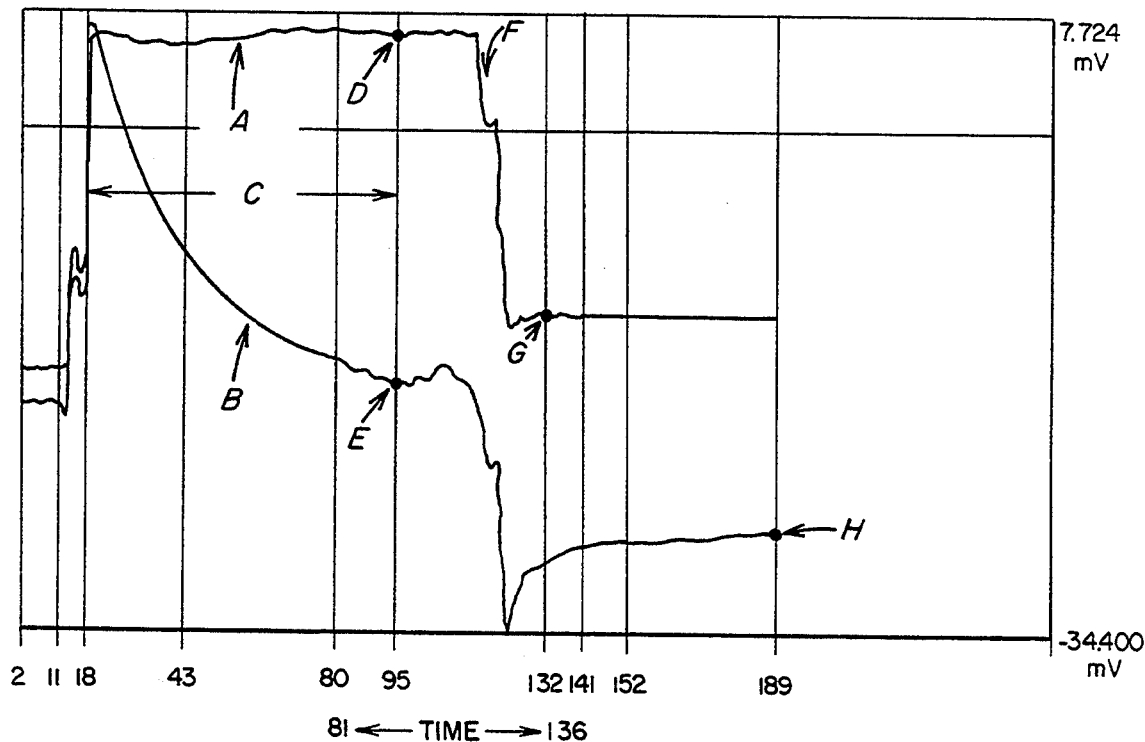
FIG. 5 is a graph of the millivolts (mV) along the ordinate versus time in seconds along the abscissa for the analysis of two analytes, carbon dioxide and hydrogen ion (pH) for a blood sample.

The program takes the data and the aforementioned relationships and utilizes them as illustrated in FIG. 5 and Table 1 to give data for the analysis of the preferred embodiment of the present invention. Preferably, carbon dioxide and the pH of a blood sample is measured. In FIG. 5, "A" indicates the millivolts per second for the pH sensor and "B" indicates the millivolts per second for the carbon dioxide sensor. Time period "C" indicates the calibration period during which time a calibration fluid with known values of pH and carbon dioxide are presented to the two analyte electrodes, one for carbon dioxide and one for pH, on the substrate 11 like that of FIGS. 1, 1b or 2 and 2b. Preferably, the measurement is taken at a temperature comparable to body temperature and the heater and thermistor and resistor arrangement of the substrate 11 control this temperature.

In FIG. 5, point "D" and point "E" indicate the initial values for the pH and carbon dioxide, respectively. These values are recorded for later use. At point "F" in FIG. 5, the sample of blood is in the fluid circuit in contact with the analyte electrodes. Points "G" and "H" indicate the final values for the pH and carbon dioxide, respectively. These final values are also recorded.

Table 1 shows the calibrant values and the sample values at points "D", "E", "F" and "G" and also shows the calculated values from the formulas for the blood sample.

The time line for the analysis cycle shown in FIG. 5 includes connecting the substrate with electrodes to the analyzing means 116 as the aforedescribed a programmed computer means and within about five seconds taking the pH and carbon dioxide millivolt readings for the storage fluid. After a period of time greater than 15 seconds, a calibration fluid is passed over the analyte electrodes. Twenty-four seconds after the calibration fluid contacts the electrodes, the calibration pH and carbon dioxide millivolt readings are taken at room temperature. A second later the sensor is heated by the heater 68 on the substrate 11 and for about 10 seconds the thermistor stabilizes and the calibrant pH and the carbon dioxide millivolt readings are taken. Within a second or so the blood sample contacts the analyte electrodes and the thermistor stabilizes over a short period of time (in seconds) and the pH and carbon dioxide millivolt readings are taken for the blood sample within 60 seconds from the blood contacting the analyte electrodes.

TABLE 1

|  | Calibrant | Sample | Calibrant Values | Blood Values |
|---|---|---|---|---|
| pH | 6.6 mV | 13.0 mV | 7.185 | 7.470 |
| $CO_2$ | −17.3 mV | −27.7 mV | 57.3 | 36.3 |

Peak = 17.022, 7.724)
$CO_2$ = 50.59
Room Temperature = 23.06
Sensor OK!
mV $CO_2$ = ($CO_{2f}$ − $CO_{2i}$) = (−27.7 − (−17.3)) = −10.4 mV
mV pH = ($pH_f$ − $pH_i$) = (−13.0 − 6.6) = −19.6 mV $$CO_{2f} = CO_{2i} * 10 \uparrow \frac{-(SEN[CO_2][pH])(mVpH) - (SEN[pH][pH])(mVCO_2)}{-(SEN[CO_2][pH])(SEN[pH][CO_2]) + (SEN[pH][pH])(SEN[CO_2][CO_2])}$$

= 36.3 mm Hg $$pH_f = \frac{-mVpH + SEN[pH][CO_2] * LOG\ CO_{2f}/CO_{2i}}{-SEN[pH][pH]} + pH_i = 7.470$$

where:
SEN[pH][$CO_2$] = sensitivity of the pH electrode favoring the $CO_2$ analyte
SEN[pH][pH] = sensitivity of the pH electrode favoring the $H^+$ analyte for the second analyte
SEN[$CO_2$][pH] = sensitivity of the $CO_2$ electrode favoring the $H^+$ analyte
SEN[$CO_2$][$CO_2$] = sensitivity of the $CO_2$ electrode favoring the $CO_2$ analyte
f = final measurement
i = initial measurement

We claim:
1. A combined electrochemical sensor assembly for measuring coupled analytes, comprising:
a) means for holding the electrodes in space apart, insulated relationship and in electrical conducting contact with electrical circuitry for each electrode, where the means is a nonconducting substrate;
b) a first electrode mounted on the substrate for electrical connection to an external lead from the substrate and positioned to contact sample fluid, wherein the electrode has: a conductor electrically connected to electrical circuitry, an ion selective membrane selective for permeation by a first analyte of the coupled analytes and electrolyte that maximizes the electronic response of the first analyte and that minimizes the electric response of the second analyte of the coupled analytes in converting the ionic potentials to electronic potentials and;
c) a second electrode mounted on the substrate for electrical connection to an external lead from the substrate and in spaced apart relation to the first electrode and positioned to contact sample fluid, wherein the second electrode has; a conductor electrically connected to electrical circuitry, an ion selective membrane, and an electrolyte to maximize the electronic response of the other analyte in the coupled multi-analytes while minimizing the electronic response of the first analyte in the conversion of the ionic potentials of the multi-analytes to electronic potentials, wherein both electrodes give some electronic response for both analytes, wherein the membranes for each electrode have a first and second side and the membrane is positioned in the electrode for one side to be in contact with the electrolyte of that electrode and the other side available for exposure to analyte-containing fluids and calibration fluids for analysis and the membrane holds the electrolyte in contact with the electrodes and provides for entry of the analyte into the electrolyte;

d) reference electrode mounted on the substrate for electrical connection to an external lead from the substrate and in spaced apart relation to the first and second electrodes and positioned to contact the sample fluid;

e) electric circuitry on the substrate to electrically connect the electrodes to an external lead from the substrate for conveyance of electrical potentials and for electrical connection of the reference electrode to the first and second electrodes;

f) fluid circuit in liquid contact with the first, second and reference electrodes and insulated from the conductive pathways from the electrodes and from any external leads from the substrate;

g) analyzing means electrically connected to the external leads of the substrate to receive the electrical potentials from the electrodes and to calculate the numerical values from simultaneous equations as follows:

$$\text{delta } mVA1 = -SE1A1 \times \text{delta pH} - SE1A2 \times \log A2f/A2i \qquad \text{Equation 1}$$

$$\text{delta } mVA2 = -SE1A2 \times \text{delta pH} - SE2A2 \times \log A2f/A2i \qquad \text{Equation 2}$$

$$A2f = A2i \times 10^n \qquad \text{Equation 3}$$

where $$n = \frac{[SE2A1 \times \text{delta } mVA1 - SE1A1\ \text{delta } mVA2]}{[-SE2A1 \times SE1A2 + SE1A1 \times SE2A2]}$$

$$A1f = \text{delta } mVA1 + \frac{SE1A2 \times \log A2f/A2i}{-SE1A1} + A1i \qquad \text{Equation 4}$$

where:
delta mV = change in millivolts
A1 = first analyte
A2 = second analyte
E1 = electrode constructed to favor the first analyte
E2 = electrode constructed to favor the second analyte
SE1A1 = sensitivity of the electrode favoring the first analyte for the first analyte
SE1A2 = sensitivity of the electrode favoring the first analyte for the second analyte
SE2A1 = sensitivity of the electrode favoring the second analyte for the first analyte
SE2A2 = sensitivity of the electrode favoring the second analyte for the second analyte
f = final measurement
i = initial measurement.

2. The apparatus of claim 1, wherein the first electrode and second electrodes have polymeric membranes from a gas permeable polymer having a molecular weight range in weight average molecular weight in the range of around 10,000 to around 500,000 but the membrane of one of the electrodes is from a polymer with a molecular weight lower than that for the membrane of the other electrode.

3. The apparatus of claim 1, wherein the first electrode and second electrodes have polymeric membranes from a gas permeable polymer having a similar molecular weight of that in the range of weight average molecular weights of around 10,000 to around 500,000.

4. The apparatus of claim 2, wherein the gas permeable polymeric membranes are selected from the group consisting of: poly(vinylchloride), poly(bisphenol-A carbonate), cellulose acetate, poly(methylmethacrylate), poly(vinylidene chloride), polystyrene, polyurethane, block copolymers of polysiloxane/poly(bisphenol-A carbonate), polymers and copolymers of lower alkyl acrylate and methacrylate, and silicone rubber.

5. The apparatus of claim 4, wherein the electrolytes are aqueous based.

6. The apparatus of claim 1, wherein the first electrode has an electrolyte that favors the conversion of the ionic potential to electronic potential of one analyte over a second analyte while the second electrode has an electrolyte that favors the conversion of ionic potential to electronic potential for the second analyte over the first while both electrodes have sensitivities for both analytes.

7. The apparatus of claim 1, wherein the analyzing means is a programmed computer means having the functions of analog input processing, analog to digital conversion, programmed microprocessing, and a date/time circuit and battery backup random access memory, and a power supply.

8. The combined pH and carbon dioxide sensor system, comprising:
    a) nonconducting substrate suitable for carrying printed wiring circuits;
    b) pH electrode mounted on the substrate for electrical connection to an external lead from the substrate and to contact sample fluid, wherein the electrode has an ion selective gas permeable polymeric membrane and an electrolyte to minimize the electronic response of the carbon dioxide while maximizing the electronic response for the hydrogen ion in converting ionic potentials to electronic potentials;
    c) carbon dioxide electrode mounted on the substrate for electrical connection to an external lead from the substrate and in space apart relation to the pH electrode to contact sample fluid, wherein the electrode has an ion selective gas permeable polymeric membrane and an electrolyte to minimize the electronic response of the hydrogen ion while maximizing the electronic response in converting ionic potentials to electronic potentials;
    d) reference electrode mounted on the substrate for electrical connection to an external lead from the substrate and in spaced apart relation to the carbon dioxide and pH electrodes to contact the sample fluid and electrically connected to the pH and carbon dioxide electrodes;
    e) electric circuitry on the substrate to electrically connect the electrodes to an external lead from the substrate for conveyance of electrical potentials and for electrical connection of the reference electrode to the pH and carbon dioxide electrodes;
    f) fluid circuit in liquid contact with the first, second and reference electrodes and insulated from the electric circuitry of the substrate; and
    g) analyzing means electrically connected to the external leads of the substrate to receive the electrical potentials from the electrodes and to calculate the pH and carbon dioxide according to the following simultaneous equations:

$$\text{delta } mVO_2 = -(SEN[CO_2][pH])(\text{delta pH}) - (SEN[CO_2][CO_2])(\log CO_{2f}/CO_{2i})$$

$$\text{delta } mVpH = -(SEN[pH][pH])(\text{delta pH}) - (SEN[pH][CO_2])(\log CO_{2f}/CO_{2i})$$

$$CO_{2f} = CO_{2i} * 10 \uparrow \frac{-(SEN[CO_2][pH])(mVpH) - (SEN[pH][pH])(mVCO_2)}{-(SEN[CO_2][ph])(SEN[pH][CO_2]) + (SEN[pH][pH])(SEN[CO_2][CO_2])}$$

$$pH_f = \frac{-mVpH + SEN[pH][CO_2] * \log CO_{2f}/CO_{2i}}{-SEN[pH][pH]} + pH_i$$

where:
delta pH = change in pH
delta mV = change in millivolts
SEN[pH][CO$_2$] = sensitivity of the pH electrode favoring the CO$_2$ analyte
SEN[pH][pH] = sensitivity of the pH electrode favoring the H$^+$ analyte for the second analyte
SEN[CO$_2$][pH] = sensitivity of the CO$_2$ electrode favoring the H$^+$ analyte
SEN[CO$_2$][CO$_2$] = sensitivity of the CO$_2$ electrode favoring the CO$_2$ analyte
f = final measurement
i = initial measurement.

9. The apparatus of claim 8, wherein the pH and CO$_2$ electrodes have membranes from gas and water vapor permeable polymers having a molecular weight range in weight average molecular weight in the range of around 10,000 to around 500,000 but the membrane of the CO$_2$ electrode is from a polymer with a molecular weight lower than that for the membrane of the pH electrode.

10. The apparatus of claim 9, wherein the gas permeable polymeric membranes are selected from the group consisting of: poly(vinylchloride), poly(bisphenol-A carbonate), cellulose acetate, poly(methylmethacrylate), poly(vinylidene chloride), polystyrene, polyurethane, block copolymers of polysiloxane/poly(bisphenol-A carbonate), polymers and copolymers of lower alkyl acrylate and methacrylate, and silicone rubber.

11. The apparatus of claim 8, wherein the pH and CO$_2$ electrodes have membranes from gas and water vapor permeable polymers having a similar molecular weight of that in the range of weight average molecular weight of around 10,000 to around 500,000.

12. The apparatus of claim 8, wherein the carbon dioxide electrode has a pH for the electrolyte in the range of greater than 7 up to 14 and the pH electrode has a pH for the electrolyte in the range of up to around 5.

13. The apparatus of claim 8, wherein the analyzing means is a programmed computer means having the functions of analog input processing, analog to digital conversion, programmed microprocessing, and a date/time circuit and battery backup random access memory, and a power supply.

14. The apparatus of claim 8, wherein the fluid circuit is filled with a fluid selected from the group consisting of storage fluid, hydrating fluid, calibrating fluid and sample fluid and mixtures of these, wherein with such mixtures the sample fluid is in contact with the analyte electrodes.

15. The apparatus of claim 8, which includes two reference electrodes connected in series and in off axial alignment with the analyte electrodes.

16. The apparatus of claim 8, wherein $$\text{delta mVCO}_2 = -(SEN[CO_2][pH])(\text{delta pH}) - (SEN[CO_2][CO_2])(\log CO_2f/CO_2i)$$

and $$\text{delta mVpH} = -(SEN[pH][pH])(\text{delta pH}) - (SEN[pH][CO_2])(\log CO_2f/CO_2i)$$

are equal to mV $CO_2 = (CO_{2f} - CO_2)$ and mV $pH = (pH_f - pH)$.

17. The apparatus of claim 8, which includes on the substrate a heater, and thermistor and resistor arrangement to heat the substrate in the vicinity of the electrodes.

18. An apparatus of combined pH and carbon dioxide electrochemical sensors for measuring the pH and the partial pressure of carbon dioxide in fluids, comprising:

a) nonconducting substrate suitable for carrying printed wiring circuits, b) a pH electrode mounted on the substrate for electrical connection to an external lead form the substrate and positioned to contact sample fluid, wherein the electrode has a gas permeable hydrophobic ion selective polymeric membrane of high molecular weight polymer selected from the group consisting of: poly(vinylchloride), poly(bisphenol-A carbonate), cellulose acetate, poly(methylmethacrylate), poly(vinylidene chloride), polystyrene, polyurethane, block copolymers of polysiloxane/poly(bisphenol-A carbonate), polymers and copolymers of lower alkyl acrylate and methacrylate, silicone rubber with ionophores of trioctylamine and an aqueous dielectric with a pH in the range of up to around 5;

c) a carbon dioxide electrode mounted on the substrate for electrical connection to an external lead from the substrate and in spaced apart relation to the pH electrode and positioned to contact sample fluid, wherein the carbon dioxide electrode has an lower molecular weight gas permeable polymeric ion selective membrane selected from the group consisting of: poly(vinylchloride), poly(bisphenol-A carbonate), cellulose acetate, poly(methylmethacrylate), poly(vinylidene chloride), polystyrene, polyurethane, block copolymers of polysiloxane/poly(bisphenol-A carbonate), polymers and copolymers of lower alkyl acrylate and methacrylate, silicone rubber with ionophores of trioctylamine and an aqueous dielectric with a pH in the range of at greater than 7 to 14, and the difference in the pH between the electrolytes is at least 0.1, and wherein both electrodes give some electronic response for both analytes;

d) reference electrode mounted on the substrate for electrical connection to an external lead form the substrate and in spaced apart relation to the pH and carbon dioxide electrodes and positioned to contact the sample fluid and electrically connected to the pH and carbon dioxide electrodes; (for each of or common to the electrodes)

e) electric circuitry on the substrate to electrically connect the electrodes to an external lead from the substrate for conveyance of electrical potentials and for electrical connection of the reference electrode to the pH and carbon dioxide electrodes;

f) fluid circuit filled with a fluid selected from the group consisting of storage fluid, hydrating fluid, calibrating fluid and sample fluid and mixtures of these, wherein with such mixtures the sample fluid is in contact with the analyte electrodes where the fluid circuit is in liquid contact with the first, second and reference electrodes and insulated from the electric circuitry of the substrate; and g) programmed computer means having the functions of analog input processing, analog to digital conversion, programmed microprocessing, and a date/time circuit and battery backup random access memory, and a power supply electrically connected to the external leads of the substrate to receive the electrical potentials form the electrodes and to calculate the numerical values from simultaneous equations as follows:

$$\text{delta mVCO}_2 = -(SEN[CO_2][pH])(\text{delta pH}) - (SEN[CO_2][CO_2])(\log CO_2f/CO_2i)$$

$$\text{delta mVpH} = -(SEN[pH][pH])(\text{delta pH}) - (SEN[pH][CO_2])(\log CO_2f/CO_2i)$$

so that upon measuring the calibration fluid for known values of pH and CO2:

$$mV\,CO_2 = (CO_{2f} - CO_{2i}) \text{ and } mV\,pH = (pH_f - pH_i)$$

$$CO_{2f} = CO_{2i} * 10 \uparrow \frac{-(SEN[CO_2][pH])(mVpH) - (SEN[pH][pH])(mVCO_2)}{-(SEN[CO_2][pH])(SEN[pH][CO_2]) + (SEN[pH][pH])(SEN[CO_2][CO_2])}$$

$$pH_f = \frac{-mVpH + SEN[pH][CO_2] * \text{LOG } CO_{2f}/CO_{2i}}{-SEN[pH][pH]} + pH_i$$

where:
delta pH = change in pH
delta mV = change in millivolts
SEN [pH][CO$_2$] = sensitivity of the pH electrode favoring the CO$_2$ analyte
SEN[pH][pH] = sensitivity of the pH electrode favoring H+ analyte for the second analyte
SEN[CO$_2$][pH] = sensitivity of the CO$_2$ electrode favoring the H$_+$ analyte
SEN[CO$_2$][CO$_2$] = sensitivity of the CO$_2$ electrode favoring the CO$_2$ analyte
f = final measurement
i = initial measurement 19. The apparatus of claim 18, wherein the reference electrode is a silver/silver chloride in block or wound wire form.

20. The apparatus of claim 1, wherein the electrolytes are solid and the membranes are water soluble.

* * * * *